United States Patent
Saito et al.

(10) Patent No.: US 8,273,069 B2
(45) Date of Patent: Sep. 25, 2012

(54) STRETCHABLE COMPOSITE SHEET AND DISPOSABLE WEARING ARTICLE USING THE SAME

(75) Inventors: Kyota Saito, Kagawa (JP); Mariko Takeuchi, Kagawa (JP); Yusuke Kawakami, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 285 days.

(21) Appl. No.: 12/594,907

(22) PCT Filed: Apr. 2, 2008

(86) PCT No.: PCT/JP2008/056610
§ 371 (c)(1),
(2), (4) Date: Oct. 8, 2009

(87) PCT Pub. No.: WO2008/126746
PCT Pub. Date: Oct. 23, 2008

(65) Prior Publication Data
US 2010/0114051 A1 May 6, 2010

(30) Foreign Application Priority Data
Apr. 9, 2007 (JP) ................................. 2007-102054

(51) Int. Cl.
*A61F 13/15* (2006.01)
(52) U.S. Cl. ......... 604/385.24; 604/385.26; 604/385.27; 604/385.29; 604/385.3
(58) Field of Classification Search ............. 604/385.24, 604/385.26, 385.27, 385.28, 385.29, 385.3
See application file for complete search history.

(56) References Cited

U.S. PATENT DOCUMENTS
6,610,383 B1 8/2003 Morman et al.
2002/0058922 A1* 5/2002 Skog .......................... 604/389

FOREIGN PATENT DOCUMENTS
| EP | 1627639 | 2/2006 |
| JP | 4-32718 U | 3/1992 |
| JP | 6-54878 A | 3/1994 |
| JP | 06054848 | 3/1994 |
| JP | 7-231913 A | 9/1995 |
| JP | 07231913 | 9/1995 |
| JP | 08000665 | 1/1996 |

(Continued)

OTHER PUBLICATIONS

PCT/JP2008/056610 International Search Report.

(Continued)

*Primary Examiner* — Jacqueline F. Stephens
(74) *Attorney, Agent, or Firm* — Lowe, Hauptman, Ham & Berner, LLP

(57) ABSTRACT

A stretchable composite sheet used in a waist region of a disposable wearing article. The stretchable composite sheet has a stretchable sheet and a non-stretchable sheet, and the stretchable sheet is stretched. Nip roll mechanisms are respectively arranged on one end side in the stretch direction (SD) and the other end side, and the stretchable sheet is bonded to the non-stretchable sheet by the nip roll mechanisms with the stretchable sheet contracted in the direction (CD) orthogonal to the stretching direction (SD). The above processes provide the stretchable composite sheet with basic weight change regions in which the basis weight of the stretchable sheet is changed depending on stretch conditions of the stretchable sheet. The basic weight of the basic weight change regions is greater than that of a center region of the stretchable composite sheet.

17 Claims, 5 Drawing Sheets

FOREIGN PATENT DOCUMENTS

| | | |
|---|---|---|
| JP | 2002067199 | 3/2002 |
| JP | 2002242064 | 8/2002 |
| JP | 2002-533243 | 10/2002 |
| JP | 2002533243 | 10/2002 |
| JP | 2005-245789 A | 9/2005 |
| JP | 2006-89907 A | 4/2006 |
| JP | 2008-106378 A | 5/2008 |
| JP | 2008106378 | 5/2008 |
| JP | 2008253679 | 10/2008 |
| WO | 0038913 | 7/2000 |

OTHER PUBLICATIONS

Abstract of JP04-032718U.
European Search Report issued to European Patent Application No. 08739720.4, mailed Nov. 24, 2011.
Office Action issued to European Patent Application No. 08739720.4, mailed Dec. 21, 2011.
Office Action issued to Chinese Application No. 200880010542.X, mailed Apr. 5, 2012.
Notice of Reasons for Rejection issued to JP Application No. 2007-102054, mailed Mar. 27, 2012.

* cited by examiner

STRETCHABLE COMPOSITE SHEET AND DISPOSABLE WEARING ARTICLE USING THE SAME

RELATED APPLICATIONS

The present application is based on International Application PCT/JP2008/056610, filed Apr. 2, 2008 and claims priority from, Japan Application Number 2007-102054, filed Apr. 9, 2007, the disclosures of which are hereby incorporated by reference herein in their entirety.

TECHNICAL FIELD

The present invention relates to a disposable wearable article constituted of wearable members in which a stretching force is provided.

BACKGROUND ART

A shorts-shaped diaper has been conventionally known as a disposable wearable article. Wearable members of the shorts-shaped diaper have partially different stretchabilities so as to improve the suitability for the wearer and the comfort. A shorts body to which a stretching force is applied includes a pair of stretchable side segments and at least one non-stretchable segment to constitute a partially stretchable and continuous waist edge portion. Members constituting the segments are bonded together. An art including such configuration, in which the waist edge portion which is partially stretchable and continuous and the waist band which is continuous and stretchable have a stretchability substantially equal to a stretchability of the stretchable side segment, is disclosed in Japanese Unexamined Patent Application Publication No. Hei 8-665.

DISCLOSURE OF THE INVENTION

Problems to be Solved by the Invention

However, the border between the segments is evident in such conventional art and it is difficult to fit the wearers' nonuniform body shapes, even if an improvement has been made to the bonding of the stretchable side segment and the non-stretchable segment. To address such a problem, a waist band having a stretchability substantially equal to a stretchability of the stretchable side segment is added thereto to improve the suitability for the wearer's waistline. The configuration adding the stretchable waistband to the waistline portion is effective to prevent a slipping off during wearing; however, it applies an unnecessary stretching force to the wearer's waistline. The comfort may thus deteriorate. In addition, the configuration of each of the segments having a stretchable layer, and the configuration and the addition to the shorts body of the waist band member requires a larger number of component members and a more complex manufacturing procedure.

The present invention has been made in view of the foregoing problem, and aims at providing a stretchable composite sheet and a disposable wearable article using the same, requiring a smaller number of manufacturing steps; not causing local squeezing of the wearer's body with simpler configuration; and can make it easy to fit to the wearer's body shape.

Means for Solving the Problems

To solve the abovementioned problems, the present inventors have found that, when constituting a stretchable composite sheet, a region can be obtained in which a stretching force gradually changes, by: drawing a first member having a stretchability; controlling the basis weight of the first member so as to change gradually; and bonding the first member being drawn to a second member of a lower stretchability, thus leading to the completion of the present invention. Specifically, the present invention provides the following stretchable composite sheet and the following disposable wearable article using the composite sheet.

In a first aspect of the present invention, a stretchable composite sheet used for a waistline region of a disposable wearable article includes: a sheet-shaped first member which has a stretchability; and a sheet-shaped second member which is of a lower stretchability than the first member, in which a pair of edge portions of the first member drawn along a drawing direction from an end to another end of the first member, being contracted to a cross direction which is orthogonal to the drawing direction, is bonded to the second member.

In a second aspect of the present invention, the stretchable composite sheet according to the first aspect is provided, in which the first member has a region in the vicinity of an edge which has a greater basis weight than a basis weight of a central portion in the cross direction.

In a third aspect of the present invention, the stretchable composite sheet according to the first or the second aspect is provided, in which the first member has regions that are preliminarily provided with different basis weights, before being drawn.

In a fourth aspect of the present invention, a disposable wearable article having a waist opening includes a pair of joining portions formed by joining side portions of a front waistline region and a back waistline region in the waistline region; and the stretchable composite sheet according to any one of the first to third aspects used in at least one of the front waistline region and the back waistline region; in which the stretchable composite sheet is disposed so that the drawing direction thereof is a direction spanning between the pair of joining portions.

In a fifth aspect of the present invention, a disposable wearable article having a waist opening includes a pair of joining portions formed by joining side portions of a front waistline region and a back waistline region in the waistline region; and the stretchable composite sheet according to any one of the first to third aspects used in at least one of the front waistline region and the back waistline region; in which the stretchable composite sheet is disposed so that the drawing direction thereof is along the pair of joining portions.

In a sixth aspect of the present invention, the disposable wearable article as described in the fourth or the fifth aspect further includes a third member in a region in the vicinity of the waist opening, which is of a lower stretchability than the first member bonded to the second member.

In a seventh aspect of the present invention, a wearable article includes a front waistline region; a back waistline region; and a crotch region disposed between the front waistline region and the back waistline region; a stretchable composite sheet disposed in at least any one of the front waistline region and the back waistline region, obtained by recoverably drawing a sheet-shaped first member, bonding the first member being drawn with a sheet-shaped second sheet which is less stretchable than the first member, and then migrating the first member to a recovery direction; and a liquid absorbent/retentive member disposed in the crotch region, in which the basis weight distribution of the stretchable composite sheet is controlled in accordance with the degree of drawing of the first member.

Effects of the Invention

According to the present invention, a stretchable composite sheet having a stretchability variable by location can be constituted by: drawing a first member and controlling the basis weight thereof so as to change gradually; and bonding the first member, having the basis weight gradually changing, to a second member. As a result, it can be provided a stretchable composite sheet and a disposable wearable article using the same, requiring a smaller number of manufacturing steps; not causing local squeezing of the wearer's body with simpler configuration; and can make it easy to fit to the wearer's body shape.

PREFERRED MODE FOR CARRYING OUT THE INVENTION

Figure 1:
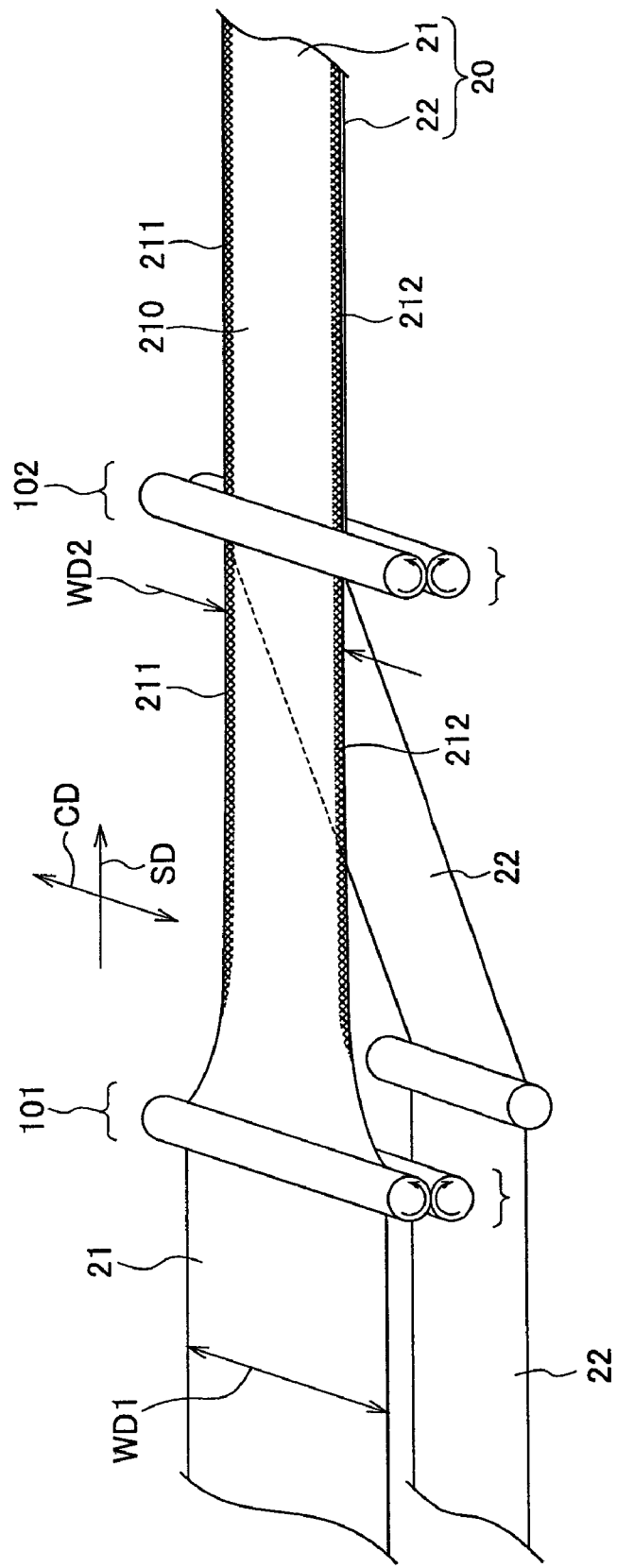
FIG. 1 is a diagram illustrating a configuration of a stretchable composite sheet according to a first embodiment of the present invention.

FIG. 1 is a diagram illustrating a configuration of a stretchable composite sheet according to a first embodiment of the present invention. The stretchable composite sheet is used for a waistline region of a disposable wearable article. A stretchable sheet 21 is an example of the sheet-shaped, stretchable first member of the present invention. The stretchable sheet 21 is, for example, a combined non-woven fabric of polyolefin fiber and elastomer fiber of 15 to 60 g/m$^2$, processed by drawing.

Conveying speed to the drawing direction of the stretchable sheet 21 is controlled by nip roll mechanisms 101 and 102 disposed at both ends of the stretchable sheet 21 in the drawing direction SD. In other words, the conveying speed of the nip roll mechanism 101 is controlled to be lower than the conveying speed of the nip roll mechanism 102, to draw the stretchable sheet recoverably. The stretchable sheet 21 being drawn is necked-in, contracted in a cross direction CD orthogonal to the drawing direction SD. This will be described in detail hereinafter.

A central portion of the stretchable sheet in the drawing direction SD, from the nip roll mechanism 101 at one end thereof to the nip roll mechanism 102 at another end thereof, is continuously affected by drawing; however, side edge portions are difficult to be affected by the drawing. Therefore, after the drawing process, the necked-in stretchable sheet 21 has the cross direction CD orthogonal to the drawing direction SD being contracted, and has altered weight regions 211 and 212 having a greater basis weight than the central portion 210.

The abovementioned necked-in stretchable sheet 21 is bonded to a non-stretchable sheet 22. The non-stretchable sheet 22 is a non-stretchable non-woven fabric, which is an example of the sheet-shaped second member of the present invention, which is of a lower stretchability than the first member. The non-stretchable sheet 22 joins the stretchable sheet 21 via the nip roll mechanism 102 and is bonded thereto by an adhesive feature provided. The stretchable sheet 21 is thus bonded to the non-stretchable sheet 22 while keeping a high-weight region in the altered weight regions 211 and 212. The non-stretchable sheet 22 restricts the drawn area of the stretchable sheet 21 and does not inhibit the restoration in the drawing direction. A stretchable composite sheet 20 is thus obtained having the high-weight region in the altered weight regions 211 and 212.

An example of the stretchable composite sheet 20 is described more specifically hereinafter. The sheet width WD1 in the cross direction CD orthogonal to the drawing direction SD of the stretchable sheet 21, before drawing, is approximately 250 mm. The sheet width WD2 of the stretchable sheet 21 which is necked-in after the drawing process or the stretchable composite sheet 20 is approximately 175 mm. In this case, the neck-in ratio (WD2/WD1) is 70%.

Regarding the altered weight regions 211 and 212, 5 to 10% of the stretchable composite sheet 20 was considered to be the region in which the basis weight and the stretching force was altered, and subjected to the measurement of the basis weight and the stretching force. The result showed that the basis weight was approximately 1 to 10% greater than the basis weight of the central portion 210. The result also showed the tendency of the basis weight in the altered weight regions 211 and 212 getting gradually greater and greater than the basis weight of the central region 210, as approaching the side edge portions from the central region 210. Thus, the altered weight regions 211 and 212 have the stretching force a few percent to ten and a few percent greater than the stretching force of the central portion 210 and the stiffness of the edge portions increases.

The neck-in ratio in the drawing process is not limited to the abovementioned value. The neck-in ratio depends on the material of the stretchable sheet 21; however, with the material of the present embodiment, preferably in the range of 50 to 80%. As described above, the high-weight region in the altered weight regions 211 and 212 can be controlled and used for designing the stretching force of the stretchable composite sheet 20.

It should be noted that, although the stretchable sheet 21 used for the stretchable composite sheet 20 of the abovementioned configuration was a sheet member having a substantially uniform basis weight before drawing, it is not limited thereto. A sheet member having regions that are preliminarily provided with different basis weights before drawing can also be used. With this configuration, the high-weight region in the altered weight regions 211 and 212 can be controlled and used for designing the stretching force of the stretchable composite sheet 20.

With the configuration of the abovementioned embodiment, it can be provided a stretchable composite sheet and a disposable wearable article using the same, requiring a smaller number of manufacturing steps; not causing local squeezing of the wearer's body with simpler configuration; and can make it easy to fit to the wearer's body shape. A disposable wearable article using the stretchable composite sheet of the abovementioned configuration will be explained hereinafter.

Figure 2:
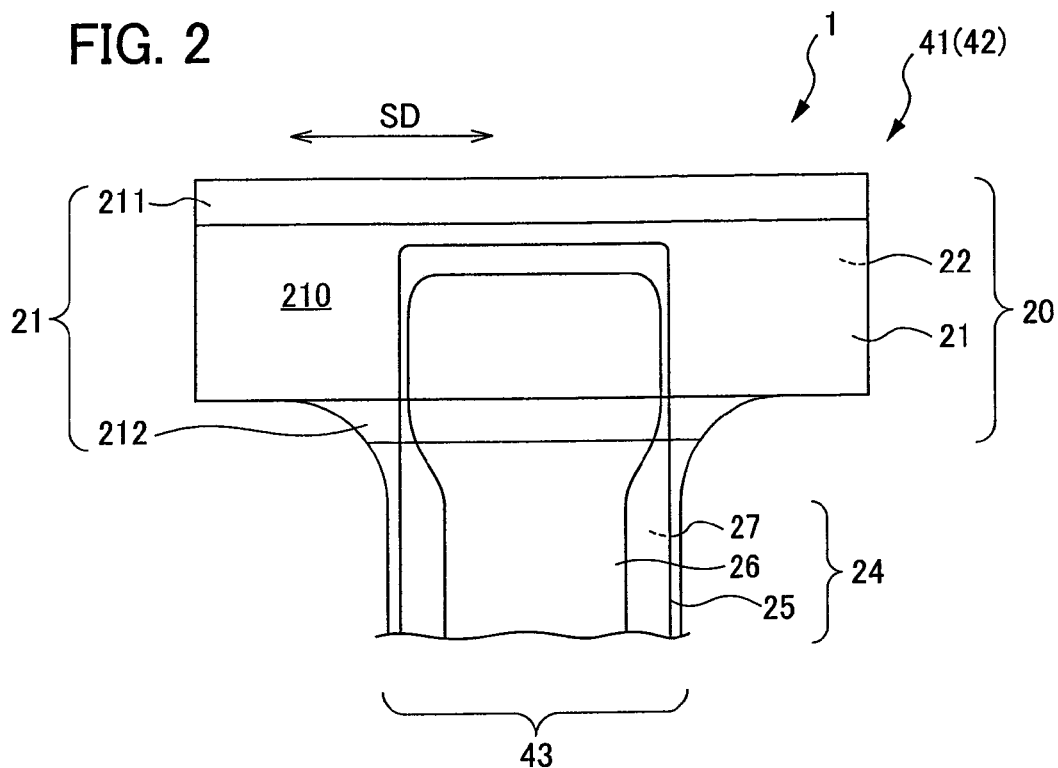
FIG. 2 is a top view of a main portion of a disposable wearable article of a second embodiment of the present invention.
Figure 3:
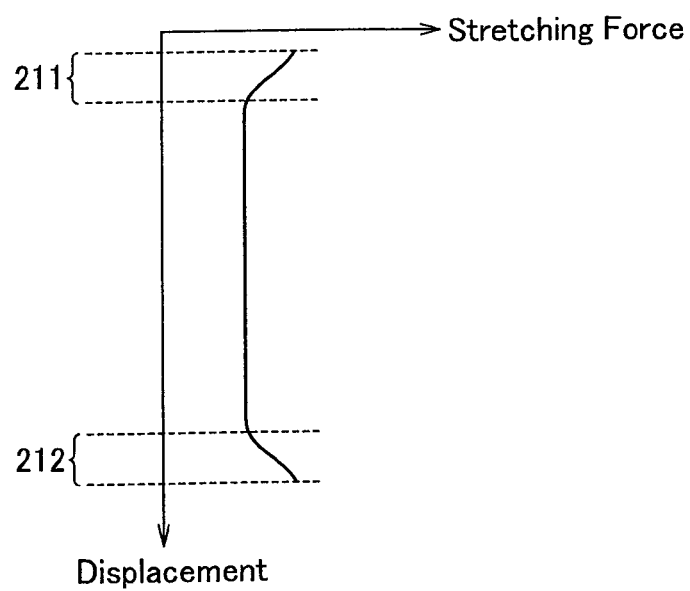
FIG. 3 is a property diagram showing a change in stretching force in accordance with displacements in a predetermined direction on the stretchable composite sheet of FIG. 2.

FIG. 2 is a top view of a main portion of a disposable wearable article of a second embodiment of the present invention. A shorts-shaped diaper is shown as an example of the disposable wearable article. As is commonly known, the shorts-shaped diaper has a front waistline region, a back waistline region, and a crotch region disposed between the front waistline region and the back waistline region. In cases in which the front waistline region and the back waistline region are flattened and spaced apart from each other, they may be referred to as chassis. The configuration showing the front waistline region with a part of the crotch region, or the back waistline region with a part of the crotch can be referred to as a chassis portion. FIG. 2 shows a chassis portion, which is a flattened state of the stretchable composite sheet constituting a diaper. The outline form, the configuration of the crotch region and the like are not limited to a particular configuration. FIG. 3 is a property diagram showing a change in stretching force in accordance with displacements in a predetermined direction on the stretchable composite sheet of FIG. 2.

The chassis portion of the shorts-shaped diaper 1 shows a front waistline region 41 with a part of a crotch region 43. The chassis portion may also be a back waistline region 42 with a part of a crotch region 43. A stretchable sheet 21 having stretchability is disposed on a surface of the chassis being a skin contacting side when formed in a shorts-like shape. The stretchable sheet 21 is bonded with the non-stretchable sheet 22, while being drawn to the drawing direction SD, as shown in FIG. 1. The non-stretchable sheet 22, which is of a lower stretchability than the stretchable sheet 21, restricts the drawn area of the stretchable sheet 21 and does not inhibit the restoration in the drawing direction. The stretchable composite sheet 20 is thus obtained. A liquid absorbent/retentive member 24 is disposed on the crotch region 43. The liquid absorbent/retentive member 24 includes a liquid permeable sheet 25, an absorbent body 26 and a liquid impermeable sheet 27. The liquid permeable sheet 25 is disposed so as to overlap with the central region of the stretchable composite sheet 20 and to include a central portion of the crotch region 43. The liquid impermeable sheet 27 is disposed so as to overlap with the liquid permeable sheet 25 and to include the central portion of the crotch region 43. Additionally, the liquid retentive absorbent body 26 is disposed between the liquid permeable sheet 25 and the liquid impermeable sheet 27.

With such configuration, the stretchable composite sheet 20 has the altered weight regions 211 and 212, in which the basis weight changes in accordance with a degree of drawing of the stretchable sheet 21. The altered weight regions 211 and 212 are disposed in the vicinity of side edge portions of the stretchable composite sheet 20. Therefore, the altered weight regions 211 and 212 have a basis weight greater than the basis weight of the central portion 210 of the stretchable composite sheet 20. Moreover, in the altered weight regions 211 and 212, the stretching force changes gradually, not drastically, as shown in FIG. 3. On the contrary, providing an elastic member such as an elastic cord or a waistband to portions requiring stretchability, the stretching force of these portions drastically changes and causes a local squeezing of the wearer's body.

It should be noted that, although FIG. 2 shows that a stretchable sheet 21, having characteristics of the present invention, is disposed on a surface of the chassis being a skin contacting side when formed in a shorts-like shape and bonded with the non-stretchable sheet 22, the present invention is not limited thereto. A non-stretchable sheet 22 can be disposed on a surface of the stretchable composite sheet 20 being a skin contacting side when formed in a shorts-like shape. Additionally, a configuration in which the non-stretchable sheets 22 are bonded to both sides of a stretchable sheet 21, having characteristics of the present invention is also possible (not shown).

Figure 4:
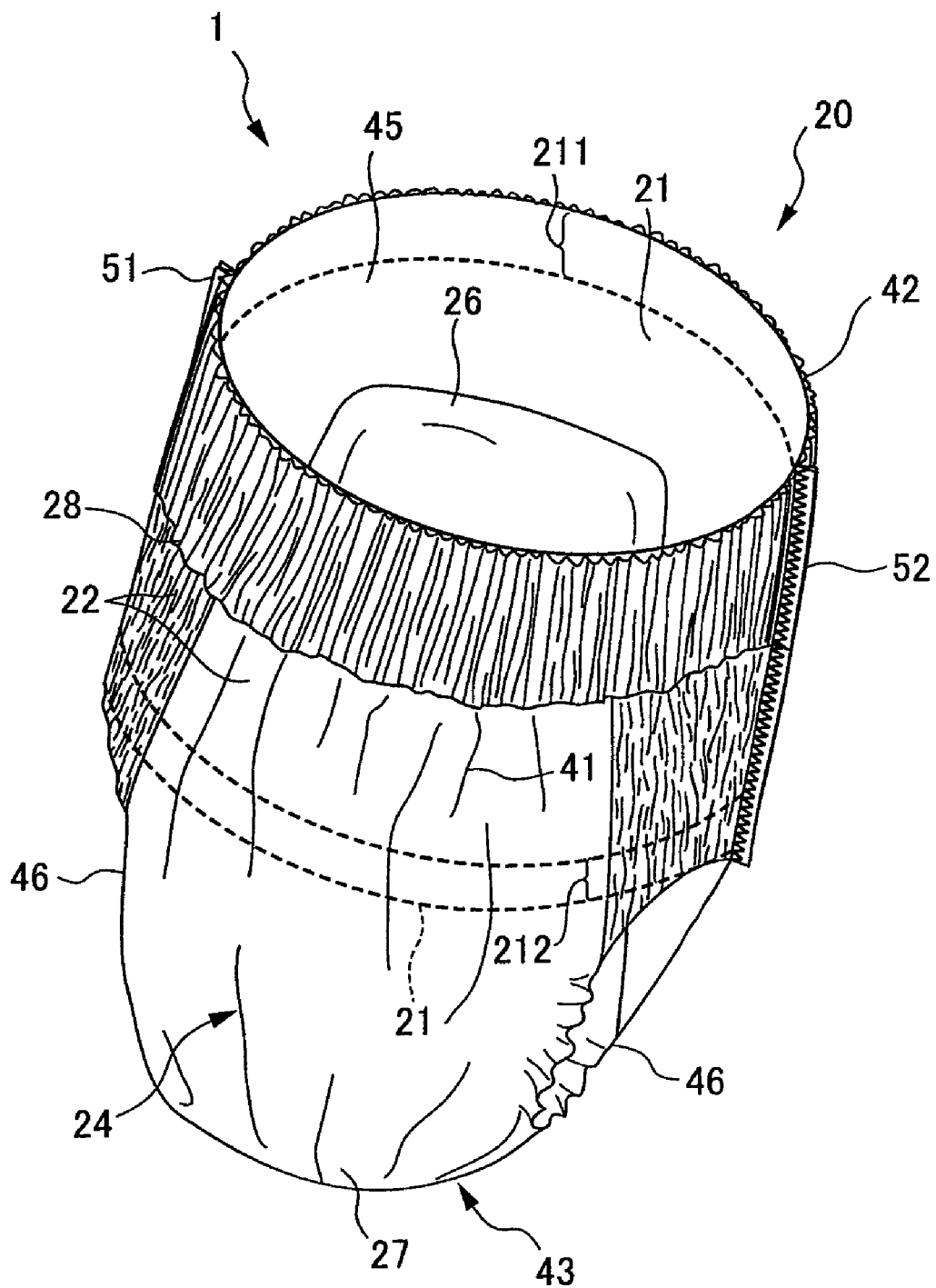
FIG. 4 is an overview of the configuration of the shorts-shaped diaper of FIG. 2.

FIG. 4 is an overview of the configuration of the shorts-shaped diaper of FIG. 2. The stretchable composite sheet 20 is disposed on the front waistline region 41 and the back waistline region 42 of the shorts-shaped diaper 1. A waist opening 45 and a pair of leg openings 46 are provided by joining side portions of the front waistline region 41 and the back waistline region 42 at a first joining portion 51 and a second joining portion 52. The stretchable composite sheet 20 is disposed so that the drawing direction thereof is a direction spanning between (across) the first joining portion 51 and the second joining portion 52. Additionally, a non-stretchable sheet 28 bonded to the non-stretchable sheet 22 is provided in the vicinity of the waist opening 45. The non-stretchable sheet 28 is not an essential component; however, it contributes to an improved strength of the waist opening 45. Even such a non-stretchable sheet 28 of a low stretchability can economically contribute to an improved strength of the waist opening 45.

In the abovementioned configuration, the stretchable sheet 21 is processed by drawing and bonded with the non-stretchable sheet 22 while controlling the degree of neck-in. The basis weight of edge portions in the width direction of the stretchable composite sheet 20, formed along the cross direction CD orthogonal to the drawing direction SD, tends to gradually increase. Thus the stretchability thereof is greater than the stretchability of the central region. In other words, stretching force is provided totally in the waistline direction of the diaper product, and stretching force gradually increasing is provided in the vicinity of the circumference of the waist opening 45 and in a region between the pair of leg openings 46. This allows a design of the stretching force suitable for the wearer's body shape. For example, the stretchable composite sheet 20 of the present invention can be applied to a part tending to be constricted in the waistline direction of the wearer's body, so as to increase the stretching force. Thus, the diaper product gives substantially no local squeezing when being worn, and can prevent leaving a depression on the wearer's skin. As a result, a disposable wearable article can be provided, requiring a smaller number of manufacturing steps; not providing a local stretching force to the wearer's body; and can make it easy to fit to the wearer's body shape.

Additionally, the basis weight and the stiffness of the region in the vicinity of the circumference of the waist opening 45 is increased, rolling up of the waist outer edge portion can be inhibited. This can eliminate the need for measures against the rolling up, such as folding back of the waist opening 45. This can cut down the number of required steps and contribute to a speeding up of the manufacture thereof.

It should be noted that, in the above-mentioned configuration, a sheet member having regions that are preliminarily provided with different basis weights before drawing can also be used as the stretchable sheet 21 in the stretchable composite sheet 20. The stretching force of predetermined portions in the stretchable composite sheet 20 can be increased by gradually changing the basis weight of the stretchable sheet 21; for example, by preliminarily increasing the basis weight of a region corresponding to the altered weight regions 211 and 212. By preliminarily changing the basis weight so as to facilitate the designation of stretching force, the further control of the basis weight is possible for the design of stretching force in the stretchable composite sheet.

Furthermore, although FIG. 4 shows the configuration in which the stretchable composite sheet 20 having characteristics of the present invention is disposed in the front waistline region 41 and the back waistline region 42, the stretchable composite sheet 20 having characteristics of the present invention can be disposed in any one of the front waistline region 41 and the back waistline region 42. In this case, the front waistline region 41 without the altered weight regions 211 and 212 or the back waistline region 42 without the altered weight regions 211 and 212 is provided, depending on the configuration.

Figure 5:
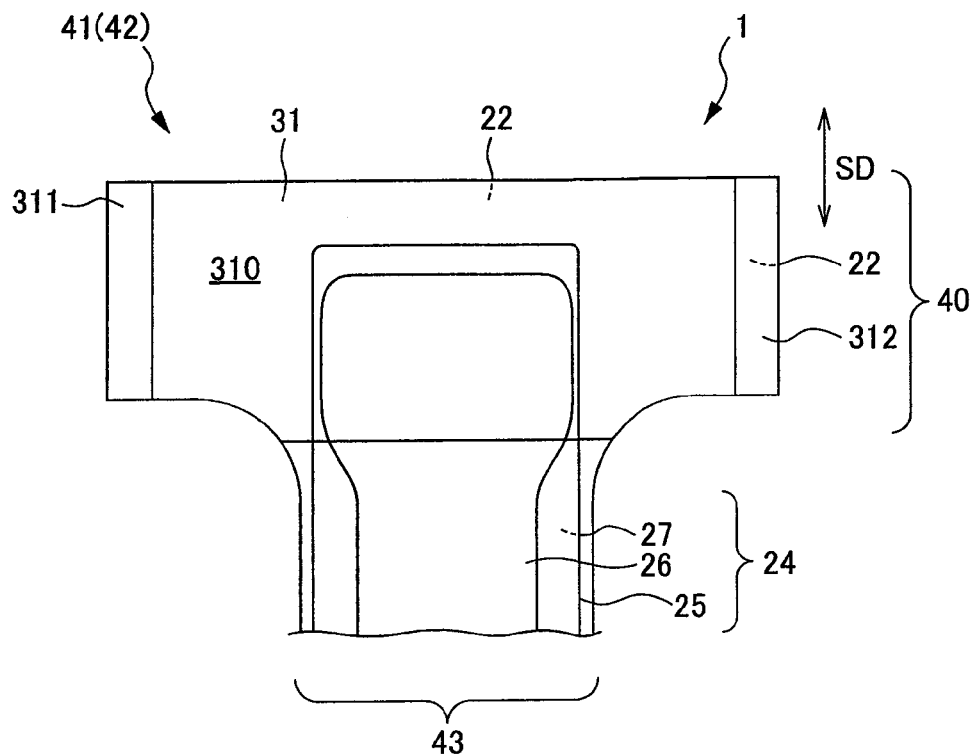
FIG. 5 is a top view of a main portion of a disposable wearable article of a third embodiment of the present invention.
Figure 6:
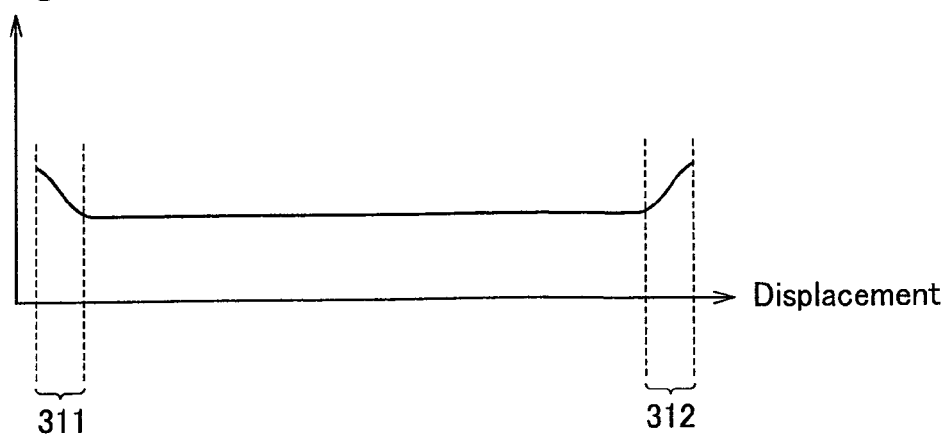
FIG. 6 is a property diagram showing a change in stretching force in accordance with displacements in a predetermined direction on the stretchable composite sheet of FIG. 5.

FIG. 5 is a top view of a main portion of a disposable wearable article of a third embodiment of the present invention. A shorts-shaped diaper is shown as an example of the disposable wearable article. FIG. 5 also shows a chassis portion, as in FIG. 2, which is a flattened state of the stretchable composite sheet constituting a diaper. The components identical to those described in FIG. 2 are designated with the same reference numerals and the detailed description will not be repeated. FIG. 6 is a property diagram showing a change in stretching force in accordance with displacements in a predetermined direction on the stretchable composite sheet of FIG. 5.

The configuration of FIG. 5 is different from FIG. 2 in that a stretchable sheet 31 is used instead of the stretchable sheet 21. The arrangement of the stretchable sheet 31 is 90 degree rotated from the arrangement of the stretchable sheet 21. The chassis portion of the shorts-shaped diaper 1 shows a front waistline region 41 with a part of a crotch region 43. The chassis portion may also be a back waistline region 42 with a part of a crotch region 43. A stretchable sheet 31 having stretchability is disposed on a surface of the chassis being a skin contacting side when formed in a shorts-like shape. The stretchable sheet 31 is bonded with the non-stretchable sheet 22, while being drawn to the drawing direction SD, as with the stretchable sheet 21 shown in FIG. 1. The non-stretchable sheet 22, which is of a lower stretchability than the stretchable sheet 31, restricts the drawn area of the stretchable sheet 21 and does not inhibit the restoration in the drawing direction. The stretchable composite sheet 40 is thus obtained.

With such configuration, the stretchable composite sheet 40 has the altered weight regions 311 and 312, in which the basis weight changes in accordance with a degree of drawing of the stretchable sheet 31. The altered weight regions 311 and 312 are disposed in the vicinity of side edge portions of the stretchable composite sheet 40. Therefore, the altered weight regions 311 and 312 have a basis weight greater than the basis weight of the central portion 310 of the stretchable composite sheet 40. Moreover, in the altered weight regions 311 and 312, the stretching force changes gradually, not drastically, as shown in FIG. 6. On the contrary, providing an elastic member such as an elastic cord or a waistband to portions requiring stretchability, the stretching force of these portions drastically changes and causes a local squeezing of the wearer's body.

It should be noted that, although FIG. 5 shows that a stretchable sheet 31, having characteristics of the present invention, is disposed on a surface of the chassis being a skin contacting side when formed in a shorts-like shape and bonded with the non-stretchable sheet 22, the present invention is not limited thereto. A non-stretchable sheet 22 can be disposed on a surface of the stretchable composite sheet 40 being a skin contacting side when formed in a shorts-like shape. Additionally, a configuration in which the non-stretchable sheets 22 are bonded to both sides of a stretchable sheet 31, having characteristics of the present invention is also possible (not shown).

Figure 7:
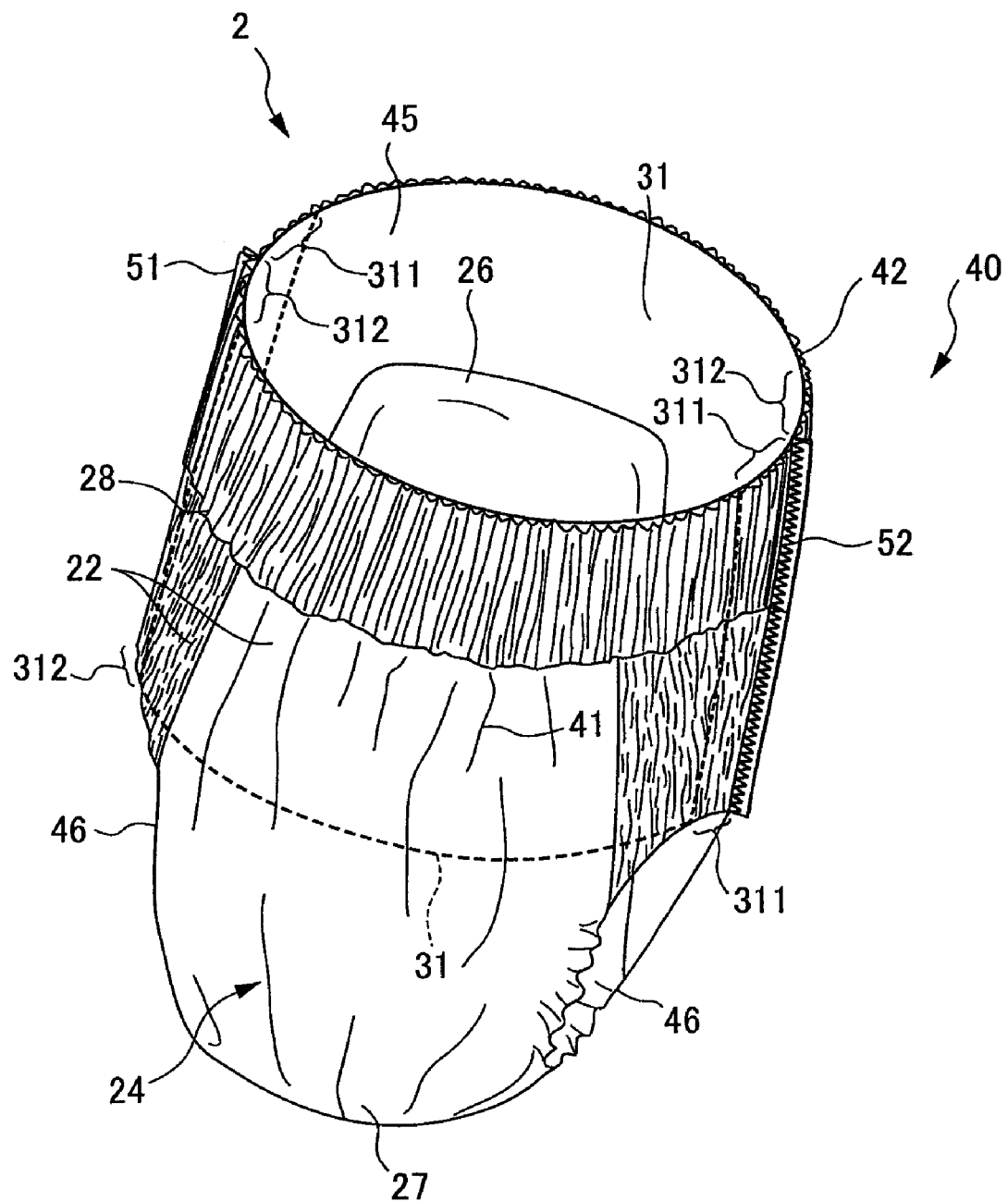
FIG. 7 is an overview of the configuration of the shorts-shaped diaper of FIG. 5.

FIG. 7 is an overview of the configuration of the shorts-shaped diaper of FIG. 5. The stretchable composite sheet 40 is disposed on the front waistline region 41 and the back waistline region 42 of the shorts-shaped diaper 2. A waist opening 45 and a pair of leg openings 46 are provided by joining side portions of the front waistline region 41 and the back waistline region 42 at a first joining portion 51 and a second joining portion 52. The stretchable composite sheet 40 is disposed so that the drawing direction thereof is along a pair of joining portions between the first joining portion 51 and the second joining portion 52. The altered weight regions 311 and 312 include regions in the vicinity of the junction between the side edge portions of the front waistline region 41 and the back waistline region 42.

In the abovementioned configuration, the stretchable sheet 31 is processed by drawing and bonded with the non-stretchable sheet 22 while controlling the degree of neck-in. The basis weight of edge portions in the width direction of the stretchable composite sheet 40 orthogonal to the drawing direction SD, tends to gradually increase. Thus the stretching force thereof is greater than the stretching force of the central region. In other words, stretching force is provided totally in the waistline direction of the diaper product, and stretching force gradually increasing is provided in the vicinity of the first joining portion 51 and the second joining portion 52. This allows a design of the stretching force suitable for the wearer's body shape. For example, the stretchable composite sheet 20 of the present invention can be applied to a part tending to be expanded in the waistline direction of the wearer's body, so as to increase the stretching force. Thus, the diaper product gives substantially no local squeezing when being worn, and can prevent leaving a depression on the wearer's skin. As a result, a disposable wearable article can be provided, requiring a smaller number of manufacturing steps; not providing a local stretching force to the wearer's body; and providing an improved adhesion to the wearer's body shape.

The shorts-shaped diaper 2 of the above-mentioned configuration provides the following operation and effect, since the side edge portions of the diaper (the first joining portion 51 and the second joining portion 52) have stretching force greater than that of the central portion, in which the liquid absorbent/retentive member 24 is disposed.

First, an operation and effect regarding the stretching force in a horizontal direction (waistline direction) of the stretchable sheet 31. The stretching property shown in FIG. 6 pulls an arbitrary part in the central portion of the diaper, in which the liquid absorbent/retentive member 24 is disposed, from the vicinity of side portions of the diaper. This draws out the liquid absorbent/retentive member 24 toward the side portions of the diaper. This makes a substantial effective area of the absorbent body 6 greater, while not making a skin contacting area of the liquid absorbent/retentive member 24 smaller. This provides a greater area for catching urine, which contributes to an improved absorbent property. Additionally, twist and displacement of the absorbent body 26 due to movements of the wearer's body during wearing can be inhibited. Furthermore, corrugation can be inhibited since the contraction of the liquid absorbent/retentive member 24 is prevented, thus providing an improved appearance.

Second, an operation and effect regarding the stretching force in a vertical direction (thickness direction of the diaper being flattened) of the stretchable sheet 31. The stretching force pulls an arbitrary part in the central portion of the diaper, in which the liquid absorbent/retentive member 24 is disposed, from the vicinity of side portions of the diaper. The stretching force in the vicinity of the side portions of the diaper improves the adhesion thereof to the wearer's body. On the other hand, the stretching force of the central portion in which the liquid absorbent/retentive member 24 is disposed is small. The effect of thrusting the absorbent body against the wearer's body is thus lowered, to allow space for catching the stool and the loose stool. This also prevents the absorbent body 26 retaining the absorbed urine from contacting the wearer's body.

It should be noted that, in the above-mentioned configuration, a sheet member having regions that are preliminarily provided with different basis weights before drawing can also be used as the stretchable sheet 31 in the stretchable composite sheet 40. The stretching force of predetermined portions in the stretchable composite sheet 40 can be increased by gradually changing the basis weight of the stretchable sheet 31; for example, by preliminarily increasing the basis weight of a region corresponding to the altered weight regions 311 and 312. By preliminarily changing the basis weight so as to facilitate the design of stretching force, the further control of the basis weight is possible for the designation of stretching force in the stretchable composite sheet.

Furthermore, although FIG. 8 shows the configuration in which the stretchable composite sheet 40 having characteristics of the present invention is disposed in the front waistline region 41 and the back waistline region 42, the stretchable composite sheet 40 having characteristics of the present invention can be disposed in any one of the front waistline region 41 and the back waistline region 42. In this case, the front waistline region 41 without the altered weight regions 311 and 312 or the back waistline region 42 without the altered weight regions 311 and 312 is provided, depending on the configuration.

The invention claimed is:

1. A stretchable composite sheet for use as a waistline region of a disposable wearable article, said stretchable composite sheet comprising:
   a first member which is a sheet that has a stretchability; and
   a second member which is a sheet of a lower stretchability than the first member,
   wherein the first member has a pair of edge portions opposite to each other in a cross direction and bonded to the second member in a thickness direction while the first member is drawn along a drawing direction orthogonal to the cross direction from an end to another end of the first member and contracted in the cross direction.

2. The stretchable composite sheet according to claim 1, wherein
   the first member has
      intermediate portions in the vicinity of the edge portions, and
      a central portion between the intermediate portions, and
   said intermediate portions have a basis weight greater than that of the central portion.

3. The stretchable composite sheet according to claim 2, wherein said intermediate and central portions of the first member are free of direct bonding to the second member.

4. The stretchable composite sheet according to claim 1, wherein the first member has regions that are preliminarily provided with different basis weights, before being drawn.

5. A disposable wearable article having a waist opening, said disposable wearable article comprising:
   front and back waistline regions, which define together the waist opening and at least one of which includes the stretchable composite sheet according to claim 1;
   a pair of joining portions joining side portions of the front and back waistline region,
   wherein the stretchable composite sheet is disposed so that the drawing direction is along a direction spanning between the pair of joining portions.

6. The disposable wearable article according to claim 5, further comprising a third member in the vicinity of the waist opening, wherein the third member is of a lower stretchability than the first member and is bonded to the second member.

7. The disposable wearable article according to claim 6, wherein
   the first member of the stretchable composite sheet is disposed on a skin-contactable side of the article,
   the second member of the stretchable composite sheet is disposed on a skin-noncontactable side of the article, and
   the third member is attached to the front and back waistline regions on a skin-noncontactable side of the second member.

8. The disposable wearable article according to claim 5, wherein the front and back waistline regions are free of elastic cords.

9. The disposable wearable article according to claim 5, wherein
   the front waistline region or the back waistline region that includes the stretchable composite sheet further includes
      a first portion in a vicinity of the waist opening,
      a second portion opposite to the first portion in the cross direction, and
      a third portion between the first and second portions, and
   the first and second portions have a basis weight greater than that of the third portion.

10. The disposable wearable article according to claim 5, wherein
   the first member of the stretchable composite sheet is disposed on a skin-contactable side of the article, and
   the second member of the stretchable composite sheet is disposed on a skin-noncontactable side of the article.

11. A disposable wearable article having a waist opening, said disposable wearable article comprising:
   front and back waistline regions, which define together the waist opening and at least one of which includes the stretchable composite sheet according to claim 1; and
   a pair of joining portions joining side portions of the front and back waistline regions,
   wherein the stretchable composite sheet is disposed so that the drawing direction is along the pair of joining portions.

12. The disposable wearable article according to claim 11, wherein the front and back waistline regions are free of elastic cords.

13. The disposable wearable article according to claim 11, wherein
   the front waistline region or the back waistline region that includes the stretchable composite sheet further includes
      a central portion between the side portions in the cross direction, and
   the side portions have a basis weight greater than that of the central portion.

14. The disposable wearable article according to claim 11, wherein
   the first member of the stretchable composite sheet is disposed on a skin-contactable side of the article, and
   the second member of the stretchable composite sheet is disposed on a skin-noncontactable side of the article.

15. The stretchable composite sheet according to claim 1, wherein the first member entirely overlaps the second member in the thickness direction.

16. The stretchable composite sheet according to claim 1, wherein the pair of edge portions of the first member is directly bonded to a pair of edge portions of the second member in the thickness direction.

17. The stretchable composite sheet according to claim 1, wherein the first and second members are free of direct bonding between the edge portions.

* * * * *